United States Patent [19]

Ringold

[11] Patent Number: 4,656,134
[45] Date of Patent: Apr. 7, 1987

[54] GENE AMPLIFICATION IN EUKARYOTIC CELLS

[75] Inventor: Gordon M. Ringold, Palo Alto, Calif.

[73] Assignee: Board of Trustees of Leland Stanford Jr. University, Stanford, Calif.

[21] Appl. No.: 722,745

[22] Filed: Apr. 12, 1985

Related U.S. Application Data

[63] Continuation of Ser. No. 338,704, Jan. 11, 1982, abandoned.

[51] Int. Cl.[4] .............. C12P 19/34; C12P 21/00; C12P 21/02; C12N 15/00; C12N 5/00; C12N 1/00; C07H 21/04

[52] U.S. Cl. .............. 435/91; 435/68; 435/70; 435/172.3; 435/240; 435/317; 536/27; 935/16; 935/34; 935/36; 935/52; 935/70; 935/71; 935/79; 935/82

[58] Field of Search .............. 435/68, 70, 91, 172.3, 435/240, 241, 317; 935/16, 34, 36, 52, 70, 71, 79; 536/27

[56] References Cited

PUBLICATIONS

Schimke, "Gene Amplification and Drug Resistance", Scientific American 243:60 (Nov. 1980).
O'Hare et al., "Transformation of Mouse Fibroblasts to Methotrexate Resistance by a Recombinant Plasmid Expressing a Prokaryotic Dihydrofolate Reductase", Proc. Natl. Acad. Sci. USA 78: 1527 (1981).
Hamer et al., "Expression of the Chromosomal Mouse Beta Major-Blobin Gene Cloned in SV40", Nature 281: 35 (1979).
Ringold et al., "Co-14 Expression and Amplification of Dihydrofolate Reductase cDNA and the Escherichia coli XGPRT Gene in Chinese Hamster Ovary Cells", J. Molec. Appl. Genet. 1(3): 165 (1981).
Wigler et al., Proc. Natl. Acad. Sci. USA (1980) 77:3567–3570.
Lee et al., Nature (1981) 294:228–232.
Nunberg et al., Proc. Natl. Acad. Sci. USA (1978) 75:5553–5556.
Wahl et al., J. Biol. Chem. (1979) 254:8679–8689.

Primary Examiner—James Martinell
Attorney, Agent, or Firm—Bertram I. Rowland

[57] ABSTRACT

Method and compositions are provided for gene amplification. A DNA unit is prepared capable of replication in a eukaryotic host having tandem genes, where the first gene is capable of complementing an auxotrophic host. The auxotrophic host is transformed with the DNA unit under selective conditions requiring enhanced expression of the first gene. Hosts are then selected for amplification of the first and second genes.

9 Claims, 3 Drawing Figures

GENE AMPLIFICATION IN EUKARYOTIC CELLS

This is a continuation of application Ser. No. 338,704, filed Jan. 11, 1982, now abandoned.

BACKGROUND OF THE INVENTION

1. Field of the Invention

Molecular biology now offers opportunities to make a wide variety of polypeptides which previously were only chemical curiosities, since their isolation was dependent upon extraction from naturally occurring sources where they existed in only minute amounts. In many instances, the ability to prepare these polypeptides offers the availability of compounds which can be used widely in therapeutic treatments, such as vaccination and supplementing the inadequate production by a mammalian host of a particular hormone or other essential physiological regulator.

In addition, the techniques of hybrid DNA technology allow for probing the genetic inheritance of plants and mammals by cloning segments of the chromosome and sequencing and expressing specific genes. In preparing polypeptides and other products by hybrid DNA technology, there is an inherent inefficiency in that a substantial proportion of the energy must be employed for the maintenance and propagation of the cellular host. To increase the efficiency of production, it will generally be desirable to maximize the production of the desired product, in effect, diverting the cell's energies to the desired result, while still maintaining the viability of the cellular host. It is therefore desirable to develop new methods whereby greater proportions of the cellular energy is directed to production of the desired end product.

2. Description of the Prior Art

Wigler, et al. PNAS USA (1980) 77: 3567-3570 describes the transformation of mammalian cells with an amplifiable dominant-acting gene. Lee, et al. Nature (1981) 294: 228-232 describe glucocorticoid regulation of expression of dihydrofolate reductase cDNA in mouse mammary tumor virus chimeric plasmids. See also Numberg et al. PNAS USA (1978) 75: 5553-5556, and Wahl et al. J. Biol. Chem. (1979) 254: 8679-8689 for descriptions of gene amplification.

SUMMARY OF THE INVENTION

Novel methods and compositions are provided for enhancing the production of a desired DNA sequence and expression of the sequence. The method employs a DNA unit capable of replication in an auxotrophic eukaryotic host and includes at least two structural genes in tandem. The first gene, which complements the auxotroph, responds to selective pressure by amplification. The second and succeeding genes are the genes of interest. By transforming the auxotroph with the DNA unit and propagating the transformants under selective conditions, amplification of the desired genes is obtained.

DESCRIPTION OF THE SPECIFIC EMBODIMENTS

Figure 1:
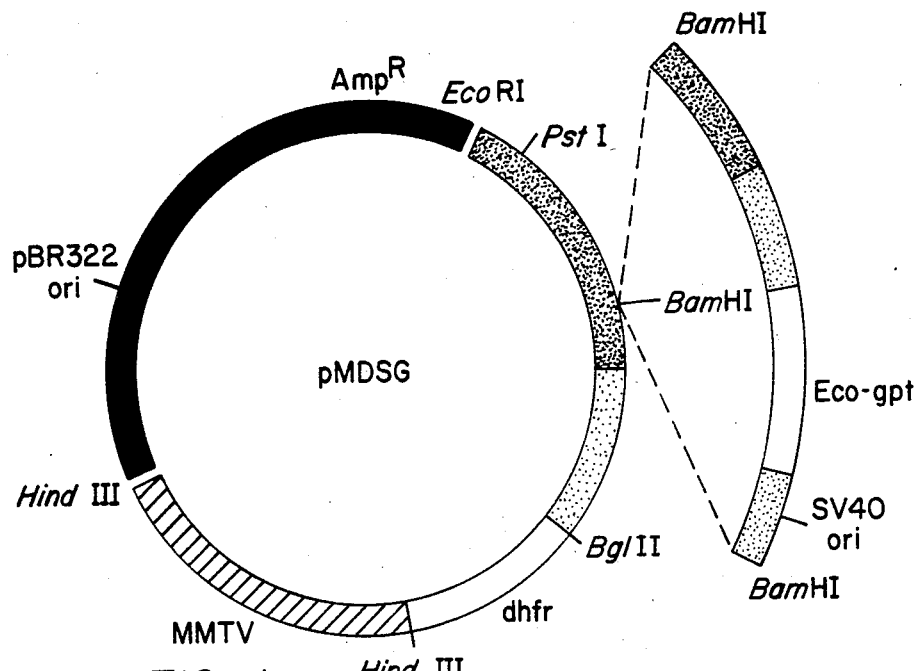
FIG. 1 depicts the plasmid pMDSG having a BamHI insert carrying the E. coli XGPRT gene and SV40 fragment.

In describing the subject invention, the DNA unit or construct will first be described which includes all of the sequences necessary for replication and amplification of a desired DNA sequence. In addition, the unit may also include numerous other sequences having a variety of functions useful for a particular application. Following the description of the unit and its method of preparation, the host will be described. This will be followed by the method employed for amplifying the desired DNA sequence.

DNA Unit

The DNA unit will include means for replication. The replication may be episomal or as part of the chromosome. For the most part, the replication sequence will provide opportunities for both, in that the unit will be capable of self-replication as an extrachromosomal unit and be capable of integration into the chromosome, either due to the presence of a translocatable sequence, such as an insertion sequence or transposon, due to substantial homology with a sequence present in the chromosome or due to non-homologous recombinational events.

The replication sequence or replicon will be one recognized by the transformed host and may be derived from any convenient source, such as from a plasmid, virus, the host e.g. an autonomous replicating segment, by itself, or in conjunction with a centromere, or the like. The particular replication sequence is not critical to the subject invention and various sequences may be employed. Conveniently, the replication sequence of a virus will usually be employed.

Critical to the subject invention is the structural gene which is referred to as the "amplifiable gene." The amplifiable gene is a structural gene which expresses a product having a function of a product also expressed by the wild strain host. It is further characterized by being able to complement an auxotrophic host and responding either to an inhibitor or lack of an essential metabolite by amplification to increase the expression product. Various genes may be employed, such as the gene expressing DHFR, the CAD gene, genes expressing metallothioneins, the gene expressing asparagine synthetase and genes expressing surface membrane proteins which offer drug resistance. By stressing the cells with enzyme inhibitors, such as methotrexate, for dihydrofolate reductase or cytotoxic agents such as metals, with the metallothionein genes, or by maintaining a low or zero concentration of an essential metabolite, the cellular response will be amplification of the particular gene and flanking sequences, particularly a downstream flanking sequence.

The DNA of interest may be any DNA sequence which is desired in multiple copies. This may be solely for the purpose of providing a ready source of a particular DNA sequence for use, for example as probes, linkers, regulatory signals, or the like. More usually, it will be desirable that the DNA sequence code for a polypeptide expression product, particularly a eukaryotic structural gene, which may be of interest or whose presence in the cell may be desirable to provide for a product. Therefore, the polypeptides may provide a wide variety of products, such as enzymes, hormones, lymphokines, interferons, immunoglobulins, the heavy and light chains or fragments thereof, surface proteins, virus capsid proteins, blood proteins, and the like. The particular product is not a significant factor in the subject invention since the coding will determine the amino acid sequence. Where the peptide of interest is small, it will usually be desirable to either have a fused polypeptide or a secretory leader sequence.

In the unit, the order of the genes and regulatory signals is in the 5'-3' direction or downstream relating to translation. The unit will have the following order: first, the promoter for the amplifiable gene; second, additional optional regulatory signals, e.g., an operator; third, the ribosomal start site; fourth, the amplifiable gene in frame with the initiation codon, and a stop site at its terminus; fifth, a terminator. The order of the signals and DNA sequences is then repeated, with the regulatory signals for transcription and translation succeeded by the DNA sequence(s) of interest, which will be referred to as succeeding sequences or genes, and the sequences of interest followed by stop sites and terminators. The initiator signals may be upstream or downstream from the terminator for the amplifiable gene.

Optional regulator signals may also be used to advantage such as CAP binding sites, activators, attenuators and the like.

The amplifiable gene and the succeeding DNA sequence of interest will usually be separated by less than about 10 kbp, more usually less than about 5 kpb and preferably less than about 2 kbp in the direction of transcription. While the amplifiable gene and the DNA sequence of interest may be transcribed in the same or different directions or have the coding (sense) strand on the same or different strands, usually they will be transcribed in the same direction and from the same strand.

Promoters will be present for both the amplifiable gene and for the succeeding or downstream DNA sequences of interest, normally structural genes. Promoters are referred to as being strong or weak depending upon the number of messenger RNA units initiated per unit time. Desirably, the promoter for the amplifiable gene should be weaker than the promoter(s) for the succeeding gene(s). In this manner, greater amplification may be achieved when applying the selective pressure with greater expression of the succeeding gene(s). Desirably, the promoter should be at least about 1.5, more preferably at least two times as strong (as defined above) for the succeeding genes as compared to the promoter for the amplifiable gene.

In conjunction with the promoter, there may be activators and operators. The activators will allow for enhanced initiation of transcription. Thus, an activator can be used in conjunction with the promoter for the succeeding genes, so that enhanced production of the desired expression products may be obtained. By contrast, the operator acts to inhibit transcription and could be used in conjunction with the promoter for the amplifiable gene. In this way, once amplification has been obtained, either endogenous or exogenous repressor could be employed to reduce or inhibit the production of the expression product of the amplifiable gene.

Usually, more than one terminator will be present, that is, the amplifiable gene will have its own terminator in between the amplifiable gene and the promoter for the succeeding genes and a terminator employed at the end of each of the succeeding genes. Preferably, there will be separate terminators for the amplifiable gene and each of the succeeding genes. The terminators should be balanced with the promoters in the sense that a strong terminator should be employed with a strong promoter.

In addition to the transcriptional regulators, there will also be translational regulators. These regulators include the Shine-Delgarno site or ribosomal binding site in proper spatial relationship with the f-met initiation codon and stop codons at the 3'-terminus of the coding strand.

The various regulatory signals may be derived from a variety of sources. Many of the signals may be already present in a generally available expression vector. Alternatively, the regulatory signals may be obtained from plasmids, viruses, chromosomes, mitochondrial DNA, or the like. A large number of regulatory signals have been isolated from a variety of sources and shown to be functionally effective outside of their natural environment. By appropriate sequencing and restriction mapping, vectors can be chosen which will have appropriate restriction sites for insertion of the regulatory signals and genes. In addition, the sequences can be modified by in vitro mutagenesis, insertion of linkers, or the like, to provide for appropriate restriction sites.

For many purposes, it will be desirable to also have a prokaryotic replication sequence in addition to a eukaryotic replication sequence. The presence of the prokaryotic replication sequence allows for amplification in a prokaryote during the preparation of the desired unit. Thus, after each in vitro modification, the resulting product may be used to transform a prokaryote, the product cloned, isolated, characterized and purified. Thus one is able to work with relatively large amounts of DNA to ensure that the sequences that have been inserted are in the proper orientation and at the proper sites.

It will also be desirable to have one or more markers to provide for selection of the desired transformants. Markers include complementation of auxotrophs, biocide resistance, e.g. antibiotic resistance, toxin resistance, heavy metal resistance, and viral immunity. Various strategies can be employed, where there are two markers permitting selection, one of which has a convenient restriction site internal to the coding strand. By selecting for the presence of one marker and the absence of the other, one can be assured of the insertion of the desired sequence into one of the markers while selecting for transformants having the other marker. The same or different markers may find use for prokaryotes and eukaryotes.

Depending upon the nature of the host, various processing genes may also be included in the DNA unit. Such genes may encode for the processing of messenger RNA, such as capping, splicing, and polyadenylation.

As previously indicated for the regulatory signals, the various genes may be derived from a wide variety of sources. In some instances, the genes may be derived from the host, while in other instances, the genes may be derived from an organism other than the host. It will frequently be desirable to have the genes derived from the same or similar family as the host, for example, employing eukaryotic genes in a eukaryotic host, more particularly, mammalian genes in a mammalian cell host.

The repetitive sequences of the amplifiable gene in tandem with the succeeding genes of interest will generally have at least five repeating units, more usually at least ten repeating units, preferably at least 25 repeating units, and may have at least 50 repeating units or more. The repetitive sequences will be interrupted by the regulatory signals intermediate the amplifiable gene and succeeding genes.

A number of different strategies may be employed for preparation of the DNA unit. For the most part, one begins with an available vector having the appropriate sequences for replication and desirably one or more markers. In addition, the vector has normally been restriction mapped, so that available restriction sites exist, which allow for insertion of DNA sequences at one or more sites without affecting other sequences which may have been inserted.

The particular order in which the various DNA sequences are introduced may be varied widely, based on the restriction sites which are present in the sequences. In some instances, it may be desirable to join one or more DNA sequences into a first vector and clone the resulting plasmid, excise the joined sequences with an appropriate restriction endonuclease and then insert the DNA fragment containing the excised sequences into a different vector at an appropriate site.

Restriction sites can be introduced by employing linkers, in vitro or site mutagenesis or appropriate tailing. Ligation can be achieved with blunt ended or staggered ended fragments, the termini depending upon the particular restriction enzyme which is employed, the manner in which the double stranded DNA is produced, or by various techniques of tailing or digestion.

There is now an extensive literature providing numerous techniques for introducing a wide variety of DNA sequences. In each instance, particular strategies will have to be developed for preparing the unit or construct having the amplifiable gene and succeeding genes with appropriate promoters. The example provided hereinafter is exemplary of a particular strategy with a particular amplifiable gene and structural gene expressing a product of interest.

A wide variety of hosts may be employed, both prokaryotic and eukaryotic. The product of interest will be expressed in a eukaryotic host, which provides various efficiencies and glycosylation capability. Desirably, cell tissue culture will be employed. Cells from vertebrates may be employed, for example, toads, mammals, such as mice, rats, rabbits, human, both healthy and oncogenic cells, such cells including gametocytes, gametes, stem cells, blast cells, and differentiated cells from various organs, including blood cells, such as lymphocytes and leukocytes, liver cells, etc. The advantage of employing higher mammalian cells is that the higher mammalian cells will efficiently recognize the particular codons of eukaryotic genes. In addition, where glycosylation is desirable, the cells will be able to glycosylate the product, so as to more closely resemble the natural product. Therefore, in many instances, it may not only be desirable but necessary to employ tissue cell cultures to obtain a product which has the desired physiological activity.

After transforming an appropriate host, the host will then be manipulated to provide for the desired amplification. The particular manner in which the amplification is achieved will vary depending upon the nature of the amplifiable gene. Where an inhibitor is used, increasing concentrations of the inhibitor may be applied to the nutrient medium of the cells. In this manner, only those cells in which the amplifiable gene is multiplied will be able to survive. One may then clone the cells and select for those cells having the highest amplification of the gene expressing the desired product. Where the gene is employed to complement an auxotroph lacking a metabolite, one can slowly diminish the amount of the required metabolite to encourage amplification of the gene expressing an essential enzyme in the metabolic sequence. Where an operator is present, the operator may be titrated with a repressor to encourage amplification. In each instance, as the amplifiable gene is amplified, the succeeding genes of interest will be amplified accordingly.

With the CAD genes, PALA may be employed as the inhibitor. With DHFR, methotrexate will be the inhibitor of choice. For the metallothionein genes, mercury salts may find use. These materials are intended to be illustrative of the various possibilities which are available.

The following examples are offered by way of illustration and not by way of limitation.

EXPERIMENTAL MATERIALS AND METHODS

Cells

Chinese hamster ovary (CHO) cells deficient in dihydrofolate reductase (DHFR) were isolated as described by Urlaub and Chasin, PNAS USA (1980) 77: 4216–4220. Growth in nonselective conditions use in Ham's F12 medium supplemented with 4% each of newborn and fetal calf serum (Irvine Scientific). Expression of the *E. coli* XGPRT gene was monitored by growth in this same medium containing 25 μg/ml of mycophenolic acid (Eli Lilly Co.) and 250 μg/ml of xanthine (Sigma). Expression of DHFR was assessed by growth in Dulbecco's modified Eagle's medium supplemented with serum (as above) and 35 μg/ml of proline.

Preparation of pMDSG

The features of the plasmid pMDSG are summarized as follows in accordance with its construction.

Figure 3:
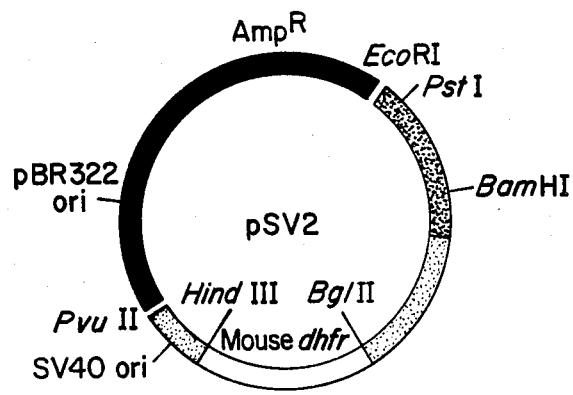
FIG. 3 is the plasmid pSV2, the salient features are as defined for FIG. 1.

The plasmid pMDSG was constructed as follows. pSV2dhfr (FIG. 3) (Subramani et. al., Molec. Cell. Biol. (1981) vol. 1 Mulligan and Berg, Science (1980) 209: 1422–1427; PNAS USA (1981) 78: 2072–2076) was digested with PvuII and HindIII adding HindIII linkers to the PvuII site. A PstI fragment located at one end of the mouse mammary tumor virus genome (MMTV) which includes the long terminal repeat (LTR) of ~1200 bp, except for about 5–10 bp at the extreme terminus, was isolated as a 1,450 bp fragment, treated with T4 DNA polymerase to remove protruding ends, and ligated to HindIII linkers. After restriction with HindIII, the modified MMTV fragment was inserted into pSV2dhfr at the newly created HindIII site to provide plasmid pMTVdhfr which was then cloned. Colonies were screened to isolate molecules containing the MMTV DNA in the appropriate orientation and pMTVdhfr isolated.

pMDSG was constructed by inserting a 2.2 kb BamHI fragment containing the SV40 origin/promoter fragment fused to Eco-gpt and SV40 RNA processing signals into the unique BamHI site of pMTVdhfr. This 2.2 kb fragment was derived by the addition of a BamHI linker to the PvuII site of pSV2gpt. (Mulligan and Berg, supra.) In FIG. 1, the solid black segment is a 2.3 kb fragment of pBR322 extending from the EcoRI site to the PvuII site that contains the β-lactamase gene (ampicillin resistance) and the origin of replication. The lightly and heavily stippled regions represent fragments derived from the SV40 DNA that provide the early promoter (linked to Eco-gpt) and RNA processing signals (a splice and a site for polyadenylation). The hatched region represents the mouse mammary tumor virus (MMTV LTR) which encompasses the promoter for viral RNA synthesis. The open regions represent either mouse DHFR cDNA or E. coli XGPRT DNA. (Mulligan and Berg, supra.) Transcription from both the MMTV promoter and the SV40 early promoter is in the counterclockwise direction, as are the coding sequences for DHFR and XGPRT. The sizes of the fragments are not drawn to scale.

DNA-Mediated Transformation of Cells

Transformation of the DHFR-deficient CHO cells with pMDSG was performed by the procedure of Graham and Van der Eb, Virology (1973) 52: 456–467, as modified by Parker and Stark, J. Virology (1979) 31: 360–369, except that carrier DNA was omitted. $10^6$ cells were exposed to a calcium-phosphate precipitate containing 10–20 μg of pMDSG and treated with 20% (vol/vol) glycerol for 5 min in PBS 4 h later. After growth for 3 days in nonselective medium, the cells was passaged (1:10) and placed into XGPRT selective medium. Colonies of transformed cells appeared approximately 10 days later and were isolated with cloning cylinders after 15–20 days.

Clone pMDSG.9 was propagated in DHFR⁻ selective medium (see above) and exposed to progressively increasing concentrations of methotrexate (Lederle). Approximately $10^6$ cells was plated in $10^{-8}$M methotrexate (MTX) and after two weeks 10–12 colonies appeared on the dish. A single colony was picked, grown to mass culture, and subsequently subjected to growth in $10^{-7}$M MTX. Again, a few colonies survived at this concentration. The resistant cells were grown to mass culture without cloning and then placed in $10^{-6}$M MTX. Cells surviving in this concentration of the drug (designated MTXR6) were used as subsequently described.

Sensitivity to the drug was analyzed by first growing cells for 3–4 generations in the absence of methotrexate, followed by addition of varying concentrations of the drug to 60 mm dishes containing $10^5$ cells. Cells were fed after 2 days and counted in a hemocytometer after 4 or 5 days. The percentage of growth inhibition was determined by comparing the number of cells present in the methotrexate-treated cultures to that in control cultures without drug.

Extracts of cells ($1-2\times 10^7$) were prepared by three cycles of freeze-thawing in liquid nitrogen and a 37° C. waterbath in a buffer containing 50 mM potassium phosphate, pH 7.4, followed by centrifugation in a microfuge for 15 min. The concentration of protein in each extract was determined by the procedure of Bradford, Anal. Biochem. (1976) 72: 248–254, with bovine γ-globulin as the standard. Varying concentrations of protein (100–300 μg from pMDSG.9 and 0.5–1.5 μg for MTXR6) were incubated with [³H]methrotrexate (Amersham, 200 mCi/mmol) for 10 min at 25° C. As described in Lee et al., supra, total protein was kept constant by addition of bovine serum albumin. The incubation mixture was passed over an 8 ml Sephadex G-50 column equilibrated in 10 mM potassium phosphate, pH 6/0.15M KCl and the counts in the excluded volume were determined in a scintillation spectrometer. Control experiments showed no binding of [³H]methotrexate to extracts from DHFR-deficient CHO cells.

DNA Extraction and Hybridization

Plasmid DNAs were isolated from E. coli by the procedure described by Hirt for isolation of polyoma DNA (Hirt, J. Mol. Biol. (1967) 26: 365–369) and centrifuged to equilibrium in cesium chloride-ethidium bromide gradients. High molecular weight chromosomal DNA for use in restriction endonuclease analyses was prepared by treatment of tissue culture cells ($1-2\times 10^8$) with sodium dodecyl sulfate (0.5%) and Pronase (500 μg/mlo) for 1 h at 37° C. Protein was removed by gentle extraction with phenol/chloroform (1:1 vol/vol) and the DNA was dialyzed exhaustively against 5 mM Tris HCl. pH 7.4/0.1 mM EDTA. Restriction endonucleases were purchased from Bethesda Research Labs and used according to BRL catalog descriptions. DNAs were cleaved with restriction endonucleases, subjected to electrophoresis through agarose gels, transferred to nitrocellulose membranes (Schleicher and Schuell) as described by Southern, ibid. (1975) 98: 503–517, and hybridized with ³²P-nick-translated pMDSG DNA or E. coli XGPRT DNA ($0.5-1\times 10^8$ cpm/μg).

Analysis of mRNA Levels

Figure 2:
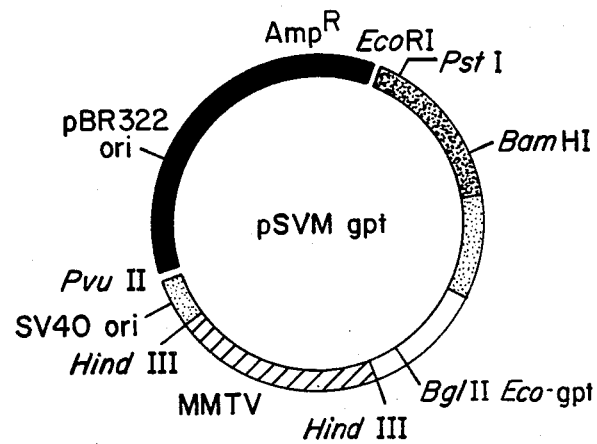
FIG. 2 is the plasmid pSVMgpt, the salient features are as defined for FIG. 1.

The relative amounts of DHFR and XGPRT RNAs present in pMDSG.9 and MTXR6 cells were estimated by hybridization of total cytoplasmic RNAs to an excess of end-labeled probes. The DNA probes were prepared as described in Lee et al., supra. The plasmids pMTV dhfr and pSVMgpt (see FIG. 2) were cut at a unique BglII site (at the end of the DHFR sequence and in the XGPRT sequence, respectively), treated with alkaline phosphatase, and labeled with [³²P]ATP employing T4 polynucleotide kinase. After digestion with EcoRI, the DNA fragments were separated by agarose gel electrophoresis and the appropriate fragments were recovered by dissolving the gel slice in 7M sodium perchlorate and adsorbing the DNA to glass powder (Volgelstein and Gillespie, PNAS USA (1979) 76: 615–619). DNA was eluted from the glass in 10 mM Tris HCl pH 7.4/0.1 mM EDTA and used for hybridizations to cytoplasmic RNAs in 80% formamide at 50° C. for 12–16 h, according to the method of Berk and Sharp, Cell (1977) 12: 721–732. Hybrids were treated with S1 nuclease (Boehringer-Mannheim) and run on non-denatured agarose (1.4%) or polyacrylamide (6%) gels respectively.

RESULTS

In the following experiments, three clones of CHO transformants were selected for functional expression of the XGPRT sequences by growth in mycophenolic acid and xanthine (Mulligan and Berg, PNAS USA (1981) 78: 2072–2076). All three of the clones were able to grow in medium lacking glycine and thymidine, indicating that the DHFR cDNA sequences were also being expressed.

Samples of whole cell DNA were cleaved with either EcoRI and HindIII (enzymes that cleave the plasmid at a single site), separated on one percent agarose gels, transferred to nitrocellulose filters and hybridized with ³²P-nick-translated pMDSG (Southern (1975), supra). One of the clones designated pMDSG.9 contained a large number of plasmid-derived sequences. The transformed phenotype is stable in the absence of selective pressure, which makes it probable that the bulk of the plasmid DNAs in the transformant is associated with chromosomal DNA. The clone pMDSG.9 was chosen for initial attempts to select MTX-resistant cells. The growth of the cell line is inhibited at MTX concentrations of $10^{-9}$ to $10^{-8}$M. The MTX-resistant cells were obtained as previously described.

Methotrexate resistance of MTXR6 and pMDSG.9 was determined at varying methotrexate concentrations. Cells (approximately $10^5$) were plated in 60 mm dishes; after 24 h, medium containing a specified concentration of methotrexate was added. Cells were fed after two days and counted in a hemocytometer five days after addition of methotrexate. The data were then graphed based on molar concentration of methotrexate versus the ratio of the number of cells observed at a predetermined concentration of methotrexate versus the number of cells in dishes containing no methotrexate. With pMDSG.9, there was no difference as to the growth of cells at about $10^{-9}$ MTX, but there was little growth at $10^{-7}$ MTX. By contrast, with MTXR6, no difference was observed between the sample and controls at $10^{-6}$ MTX, while there was substantially no growth at $10^{-4}$ MTX. Using [$^3$H]MTX as a ligand to quantitate DHFR molecules, it was estimated that the MTXR6 cells contain approximately 400 times as much DHFR as the pMDSG.9 cells.

Using the procedure of Berk and Sharp, Cell (1977) 12: 721-732, the approximate 5' end of the DHFR transcripts was determined. The major transcript in these cells (corresponds to a band at 1.1 kb in electrophoresis on a 1.4% agarose gel) appears to initiate approximately 250-300 nucleotides upstream of the DHFR insert. This is the approximate region of the 5' end of MMTV RNA and is consistent with the notion that the DHFR RNA is produced by utilization of the MMTV promoter.

The concomitant amplification of XGPRT gene was demonstrated as follows. High molecular weight DNAs from pMDSG.9 and MTXR6 cells were digested with EcoRI, run on an 0.8% agarose gel and transferred to nitrocellulose filters. The DNA filters were hybridized with either $^{32}$P-nick-translated pMDSG or $^{32}$P-nick-translated XGPRT DNA isolated by BamHI and HindIII digestion of plasmid pL10. (Mulligan and Berg, Science (1980) 209: 1423-1427). Comparison of the autoradiographs demonstrated about 50-fold increase of the XGPRT coding sequences present in MTXR6.

The amount of XGPRT RNA in pMDSG.9 and MTXR6 was quantitated as follows. A probe was prepared labeled at the BglII site of the XGPRT gene in the plasmid pSVMgpt. Since an XGPRT RNA initiating at the SV40 promoter of pMDSG has only about 125 nucleotides in common with the probe, the protected fragment will be approximately this length. The same RNAs which were used for hybridization for detection of DHFR were employed in this hybridization. The RNAs were hybridized with end-labeled XGPRT probe (25,000 cpm). Hybrids generated by S1 nuclease treatment were analyzed on a 6% acrylamide gel. The autoradiogram was exposed for 12 h. Using densitometer tracings of a number of exposures and taking into account the different inputs of RNA and hybridization, it was estimated that there was 40-60 times more XGPRT RNA in MTXR6 than in pMDSG.9 cells.

It is evident from the above results that by employing a construct having an amplifiable gene and succeeding genes expressing a product of interest, where the amplifiable gene and the succeeding genes each have a separate promoter, substantial amplification of the promoter and succeeding genes may be obtained. Furthermore, by employing an auxotroph which is complemented by the amplifiable gene, improved results in gene amplification may be obtained. By employing as the amplifiable gene, a structural gene expressing an enzyme which is essential to the production of a metabolite, particularly a metabolite required for replicating and employing an inhibitor of such enzyme, substantial gene amplification can be achieved.

Although the foregoing invention has been described in some detail by way of illustration and example for purposes of clarity of understanding, it will be obvious that certain changes and modifications may be practiced within the scope of the appended claims.

I claim:

1. A method for obtaining multiple repetitive copies of a DNA sequence of interest comprising a structural gene as continuous repetitive units which comprises:
   transforming a eukaryotic auxotrophic host cell with DNA units, said DNA units comprising:
   (1) an amplifiable structural gene complementing said auxotrophic host cell and capable of amplification upon growth of said host cell under conditions selective for prototrophy;
   (2) joined to said amplifiable structural gene, said DNA sequence of interest; and
   (3) individual regulator signals recognized by said host cell for transcription and translation of said structural gene and DNA sequence of interest, to produce transformant cells; and
   growing said transformant cells under selective conditions for said amplifiable gene;
   selecting viable cells; and
   growing in a nutrient medium said viable cells under increasingly more stringent selective conditions;
   whereby said amplifiable gene and DNA sequence of interest are amplified into multiple copies as continuous repetitive units and are expressed by said host cell.

2. A method according to claim 1, wherein said DNA becomes integrated into the chromosome of said host cell.

3. A method according any of claims 1 or 2, wherein said DNA sequence of interest codes for a eukaryotic polypeptide.

4. A method according to claim 3, wherein said polypeptide is foreign to said host.

5. A method according to any of claims 1 or 2, wherein said individual regulatory signals comprise different promoters for each of said amplifiable gene and said DNA sequence of interest, wherein said promoter for said DNA sequence of interest is stronger than the promoter for said amplifiable gene.

6. A method according to claim 3, wherein said polypeptide is an enzyme.

7. A method for producing enhanced amounts of a polypeptide, said method comprising:
   growing in appropriate nutrient medium progeny of a transformant prepared according to the method of claim 3.

8. A method according to claim 7, wherein said polypeptide is an enzyme.

9. A method according to claim 1, wherein said amplifiable structural gene codes for the enzyme dihydrofolate reductase.

* * * * *

UNITED STATES PATENT AND TRADEMARK OFFICE
CERTIFICATE OF CORRECTION

PATENT NO. : 4,656,134
DATED : April 7, 1987
INVENTOR(S) : Gordon M. Ringold

It is certified that error appears in the above-indentified patent and that said Letters Patent is hereby corrected as shown below:

Column 1, line 6, insert the following information:

--ACKNOWLEDGEMENTS

This invention was made with U.S. Government support under contract GM25821 awarded by the National Institutes of Health. The Government has certain rights in this invention.--

Signed and Sealed this

Eighth Day of July, 1997

*Attest:*

BRUCE LEHMAN

*Attesting Officer*     *Commissioner of Patents and Trademarks*